United States Patent [19]

Hagiwara et al.

[11] Patent Number: 4,480,094
[45] Date of Patent: Oct. 30, 1984

[54] BENZIL KETAL DERIVATIVES

[75] Inventors: Tsuneo Hagiwara, Hino; Akihiro Horike, Musashino, both of Japan

[73] Assignee: Teijin Limited, Osaka, Japan

[21] Appl. No.: 376,950

[22] Filed: May 11, 1982

Related U.S. Application Data

[62] Division of Ser. No. 118,238, Feb. 4, 1980, Pat. No. 4,400,519.

[30] Foreign Application Priority Data

Feb. 5, 1979 [JP] Japan .................. 54/11374

[51] Int. Cl.³ .................................. C07D 251/32
[52] U.S. Cl. .................. 544/222; 546/188; 548/310; 548/523; 548/437; 548/473; 548/478
[58] Field of Search ................................ 544/222

[56] References Cited

U.S. PATENT DOCUMENTS

| | | | |
|---|---|---|---|
| 4,145,544 | 3/1979 | Kuehn ......................... | 544/222 |
| 4,293,693 | 10/1981 | Cohen et al. .................. | 544/221 |
| 4,321,375 | 3/1982 | Cohen et al. .................. | 544/221 |
| 4,339,383 | 7/1982 | Wehner et al. ............. | 544/221 X |
| 4,400,519 | 8/1983 | Hagiwara et al. ............. | 548/461 |

Primary Examiner—Joseph Paul Brust
Attorney, Agent, or Firm—Sherman & Shalloway

[57] ABSTRACT

Benzil-di[$\beta$-(di-$\beta$-methallylisocyanuryl)ethyl]ketal of the following structural formula:

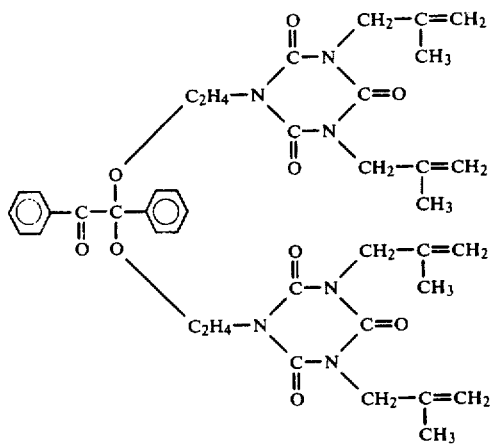

and other novel benzil ketal derivatives. The novel benzil ketal derivatives are characterized by having a structure in which an isocyanuryl-containing group is bonded to each of the two oxygen atoms of ketal. Because these compounds have a high decomposition or sublimation temperature and ability to initiate photopolymerization, they are useful as photopolymerization initiators in the production of photopolymerizable shaped articles from a molten blend of a photopolymerizable thermoplastic polymer composition.

14 Claims, No Drawings

BENZIL KETAL DERIVATIVES

This is a division of application Ser. No. 118,238, filed Feb. 4, 1980, which has issued as U.S. Pat. No. 4,400,519 on Aug. 23, 1983.

This invention relates to benzil ketal derivatives, and specifically, to thermally stable benzil ketal compounds containing an imide group or an isocyanuryl group which are useful as photopolymerization initiators.

It is well known that an unsaturated monomer, or an unsaturated polymer, or a mixture of these polymerizes photochemically in the presence of a suitable initiator such as a carbonyl compound having a halogen atom at the alpha-position of the carbonyl group, a mercaptan, a disulfide, an azo compound, benzoin, a benzoin ether, or a ketal compound of benzil.

There has recently been a significant advance in the technique of obtaining shaped articles of improved properties of melt-blending a thermoplastic saturated polymer such as a polyester, a polyamide, a polyolefin (e.g., polypropylene or polyethylene) or polystyrene with a crosslinking agent having good thermal stability such as an allyl compound (e.g., triallyl isocyanurate) and a photopolymerization initiator, shaping the resulting blend, and subsequently subjecting the shaped article to the irradiation of actinic light such as ultraviolet light U.S. Ser. No. 840,301, which has issued as U.S. Pat. No. 4,196,066 and corresponds to DOS No. 2745906.9, U.S. Ser. No. 920,834 which has issued as U.S. Pat. No. 4,256,558 and corresponds to DOS No. 2829572.9, and U.S. Ser. No. 015,798 corresponding to Dos No. 2907983.2).

These known photopolymerization initiators, however, generally have low weight loss starting temperatures (sublimation starting temperatures) or decomposition temperatures. Some of them even sublime before reaching the decomposition temperatures.

Benzophenone, a typical photopolymerization initiator, has a weight loss starting temperature of about 100° C. Benzoin ethyl ether has a weight loss starting temperature of about 130° C., and benzil dimethyl ketal has a weight loss starting temperature of about 116° C. These compounds sublime before they reach the decomposition temperatures. Accordingly, conventional photopolymerization initiators having low weight loss starting temperatures are unsuitable for use in the production of photo-polymerizable shaped articles from the aforesaid melt-blended compositions of thermoplastic polymers.

It is an object of this invention to provide a photopolymerization initiator which has a high decomposition temperature or sublimation temperature and when blended in the molten state with a thermoplastic polymer and a crosslinking agent, is not lost from the blend by decomposition or sublimation.

The present inventors made investigations in order to achieve this subject, and noted that polymers containing a cyclic imide group are resins having superior thermal stability, such as aromatic polyimides typified by Kapton ®, polyamideimides, polyesterimides, polyhydantoin, and polymaleimide. Consequently, the inventors have found that benzil ketals attain high decomposition temperatures and sublimation temperatures by introducing thereinto a cyclic imide group.

According to this invention, there is provided a benzil ketal derivative of the following general formula

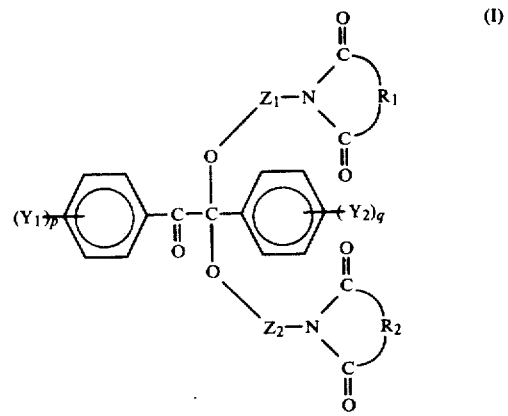

wherein $Y_1$ and $Y_2$ are identical or different, and each represents a group selected from the class consisting of a hydrogen atom, alkyl groups having 1 to 10 carbon atoms, aryl groups having 6 to 12 carbon atoms, alkoxy groups having 1 to 10 carbon atoms and halogen atoms; p and q, independently from each other, are integers of 1 to 3; $Z_1$ and $Z_2$ are identical or different and represent a divalent aliphatic hydrocarbon group having 2 to 4 carbon atoms and optionally containing an aliphatic ring or an aromatic ring; and

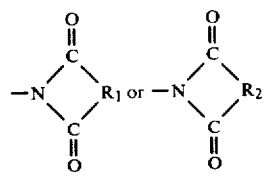

represents a substituted or unsubstituted isocyanuryl or hydantoin group, or a 5- or 6-membered cyclic imide group in which $R_1$ and $R_2$ are identical or different and represent a divalent aliphatic, alicyclic or aromatic hydrocarbon having 2 to 15 carbon atoms and optionally having a halogen atom.

In the above formula, $Y_1$ and $Y_2$, independently from each other, are preferably a hydrogen atom or an alkyl group having 1 to 10 carbon atoms, especially 1 to 5 carbon atoms. This is based on the ease of obtaining and producing starting materials.

In the above compound, the position of $Y_1$ or $Y_2$ is preferably meta or para, more preferably para. Most preferably, both $Y_1$ and $Y_2$ are hydrogen atoms.

Preferred groups $Z_1$ and $Z_2$ are alkylene groups having 2 to 10 carbon atoms, preferably 2 to 9 carbon atoms, aliphatic ether or thioether groups having 3 to 10 carbon atoms, preferably 4 to 8 carbon atoms, and divalent aralkylene groups having 8 to 20 carbon atoms, preferably 8 to 14 carbon atoms.

The divalent aralkylene groups denote divalent groups of the following formula $$-R-Ar-R'-$$

wherein Ar represents an aryl group, and —R— and —R'— are identical or different alkylene groups having 1 to 5 carbon atoms, preferably 1 or 2 carbon atoms, and —R—Ar—A'— has 8 to 14 carbon atoms, preferably 8 to 10 carbon atoms.

More preferred compounds are produced when $Z_1$ and $Z_2$ are groups of the formula $$-(CH_2)_m-Q-(CH_2)_n-$$

wherein Q represents $$-\overset{R_3}{\underset{R_4}{C}}-, \quad -\!\!\left\langle\!\!\bigcirc\!\!\right\rangle\!\!-,$$

—O—, —S—, or a bond, m and n are integers of 1 to 3, and $R_3$ and $R_4$ represent a hydrogen atom or a methyl group. Most preferably, $Z_1$ and $Z_2$ are —$C_2H_4$—, —$C_3H_6$—, and —$C_4H_8$—.

Preferred cyclic imide groups $$-N\overset{\overset{O}{\|}}{\underset{\underset{O}{\|}}{\overset{C}{\underset{C}{\diagdown}}}}\!\!R_1 \quad \text{and} \quad -N\overset{\overset{O}{\|}}{\underset{\underset{O}{\|}}{\overset{C}{\underset{C}{\diagdown}}}}\!\!R_2$$

are those in which $R_1$ and $R_2$ are expressed by the following formula $$-\overset{S_1}{\underset{T_1}{C_1}}\!\!-\!\!(\overset{S_2}{\underset{T_2}{C_2}})_r\!\!-\!\!\overset{S_3}{\underset{T_3}{C_3}}-$$

wherein r is 0 or 1, and $S_1$, $S_2$, $S_3$, $T_1$, $T_2$, and $T_3$, independently from each other, represent a hydrogen atom, a hydrocarbon group having 1 to 6 carbon atoms and optionally containing a halogen atom, or a bond, and they may be bonded to each other to form an aliphatic or aromatic ring together with $$-C\!\!-\!\!(C_2)_r\!\!-\!\!C_3-.$$

In the above definition, the "bond", for example, means one single bond in the double bond existing between $C_1$ and $C_2$ and between $C_3$ and $T_3$ or between $C_1$ and $C_3$ in the following formulae.

(r is 1 and $S_1$, $S_2$ and $S_3$ are bonds), (r=0, and $S_1$ and $S_3$ are bonds).

The groups "which are bonded to each other to form an aliphatic or aromatic ring together with $$-C_1-(C_2)_r-C_3-,$$

for example, mean the following.

Examples of more preferred cyclic imide groups $$-N\overset{\overset{O}{\|}}{\underset{\underset{O}{\|}}{\overset{C}{\underset{C}{\diagdown}}}}\!\!R_1 \quad \text{and} \quad -N\overset{\overset{O}{\|}}{\underset{\underset{O}{\|}}{\overset{C}{\underset{C}{\diagdown}}}}\!\!R_2$$

are as follows:

(R: —CH=CH—), (R: —CH$_2$—CH$_2$—), $R_6$ and $R_7$ are identical or different, and represent $C_{1-5}$ alkyl, $$-CH_2-CH=CH_2, \quad -CH_2-\overset{\overset{CH_3}{|}}{C}=CH_2$$

or $-CH_2-\!\!\left\langle\!\!\bigcirc\!\!\right\rangle$.

-continued and

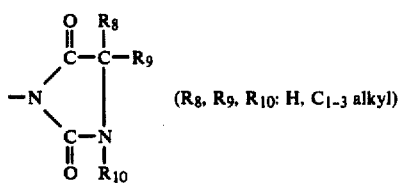

($R_8$, $R_9$, $R_{10}$: H, $C_{1-3}$ alkyl)

Specific examples of the compounds of formula (I) are given below.

1. Benzil-di-($\beta$-succinimidoethyl)ketal

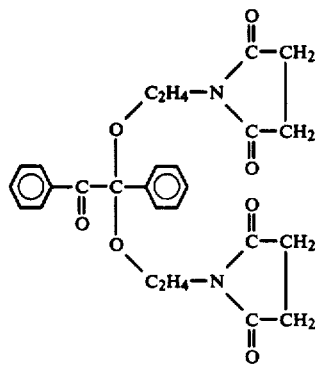

2. Benzil-di-($\beta$-phthalimidoethyl)ketal

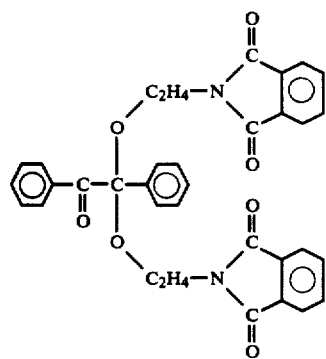

3. Benzil-di-($\beta$-glutarimidoethyl)ketal
4. Benzil-di-($\beta$-3,3-dimethylglutarimidoethyl)ketal
5. Benzil-di-($\beta$-tetrahydrophthalimidoethyl)ketal
6. Benzil-di-($\beta$-hexahydrophthalimidoethyl)ketal
7. Benzil-di-($\beta$-diallylisocyanurylethyl)ketal
8. Benzil-di-($\beta$-dimethallylisocyanurylethyl)ketal
9. p,p'-Dimethylbenzil-di-($\beta$-phthalimidoethyl)ketal
10. p,p-Dimethylbenzil-di-($\beta$-diallylisocyanurylethyl)ketal -continued

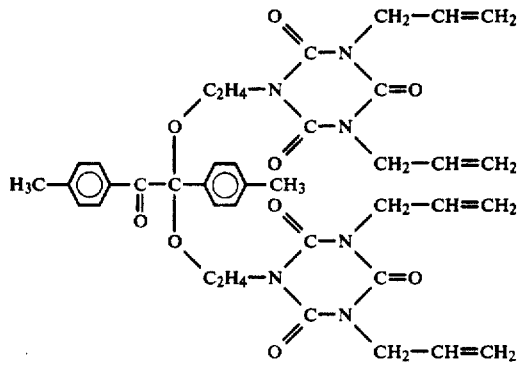

11. p,p'-Dichlorobenzil-di-($\beta$-phthalimidoethyl)ketal
12. p,p'-Dimethoxybenzil-di-($\beta$-diallylisocyanurylethyl)ketal
13. p-Methylbenzil-di-($\beta$-phthalimidoethyl)ketal
14. Benzil-di-($\beta$-dimethylisocyanurylethyl)ketal
15. Benzil-di-($\beta$-diphenylisocyanurylethyl)ketal
16. Benzil-di-($\beta$-dibenzylisocyanurylethyl)ketal

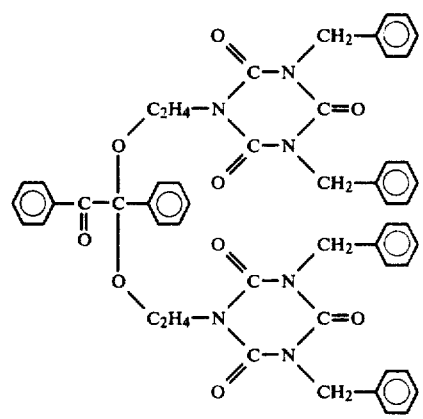

17. Benzil-di-($\beta$-methylethylisocyanurylethyl)ketal
18. Benzil-($\beta$-diallylisocyanurylethyl, $\beta$-phthalimidoethyl)ketal
19. Benzil-($\beta$-diallylisocyanurylethyl, $\beta$-dimethylisocyanurylethyl)ketal
20. Benzil-($\beta$-diallylisocyanurylethyl, $\beta$-dimethallylisocyanurylethyl)ketal

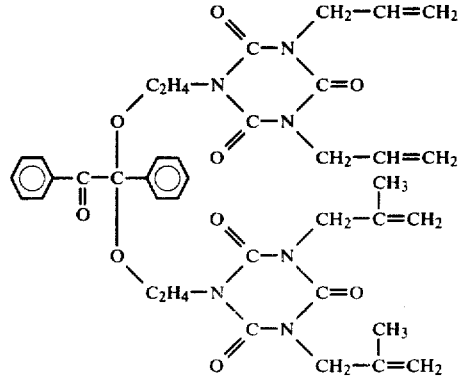

21. Benzil-di-($\gamma$-diallylisocyanurylpropyl)ketal
22. Benzil-di-($\gamma$-phthalimidopropyl)ketal
23. Benzil-di-($\delta$-diallylisocyanurylbutyl)ketal
24. Benzil-di-($\delta$-phthalimidobutyl)ketal 25.
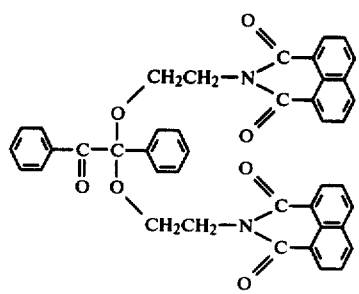

26.
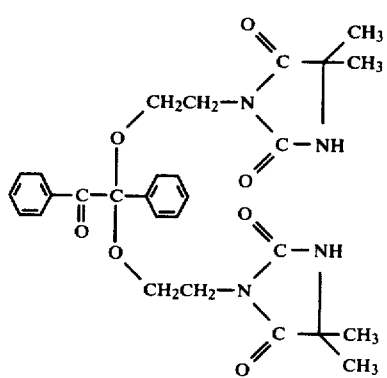

27.
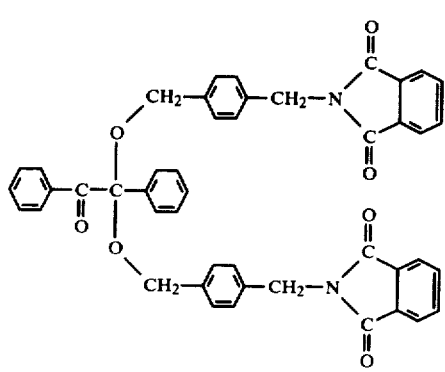

28.
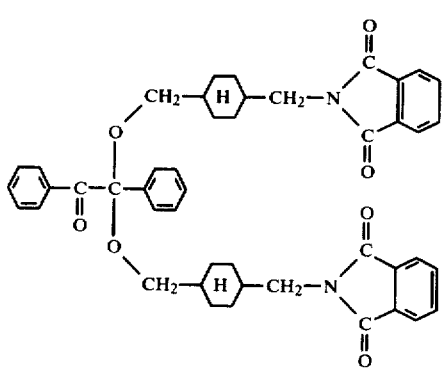

29.
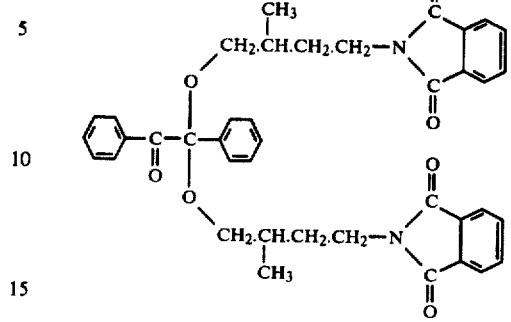

30.
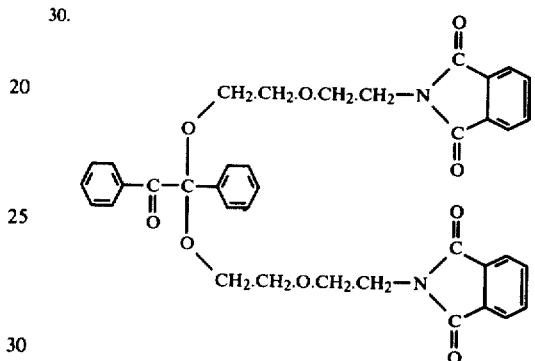

The benzil ketal derivative of this invention can be easily prepared by condensing a benzil ketal derivative of the following general formula

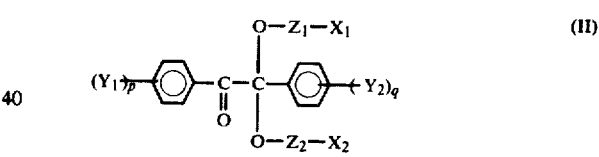

wherein $Y_1$, $Y_2$, $Z_1$, $Z_2$, p and q are the same as defined hereinabove, and $X_1$ and $X_2$ represent the same or different halogen atoms, with a compound of the following general formula

wherein M represents an alkali metal, and $R_o$ is the same as $R_1$ and $R_2$ defined hereinabove.

The above condensation reaction can be effected by simply contacting the compound of formula (II) with the compound of formula (III) at room temperature or at an elevated temperature in a suitable reaction solvent or in the absence of a solvent.

The reaction temperature is from 0° to 150° C., preferably from 20° to 100° C. Suitable reaction solvents include N,N-dimethylformamide, dimethylsulfoxide, N,N-dimethylacetamide, N-methylpyrrolidone, N,N,N',N'-tetramethylurea, hexamethylphosphoric triamide, dioxane, tetrahydrofuan, ether, ethyleneglycol-dimethylether, diethyleneglycoldimethylether, benzene, and toluene.

For example, when both $Y_1$ and $Y_2$ are hydrogen atoms, both $Z_1$ and $Z_2$ are —$C_2H_4$—, and both $R_1$ and $R_2$ are —$CH_2$—$CH_2$—, the compound of this invention can be obtained by reacting benzil-di-($\beta$-bromoethyl)-ketal with sodium succinimide in N,N-dimethylformamide, as schematically shown by the following reaction scheme (A).

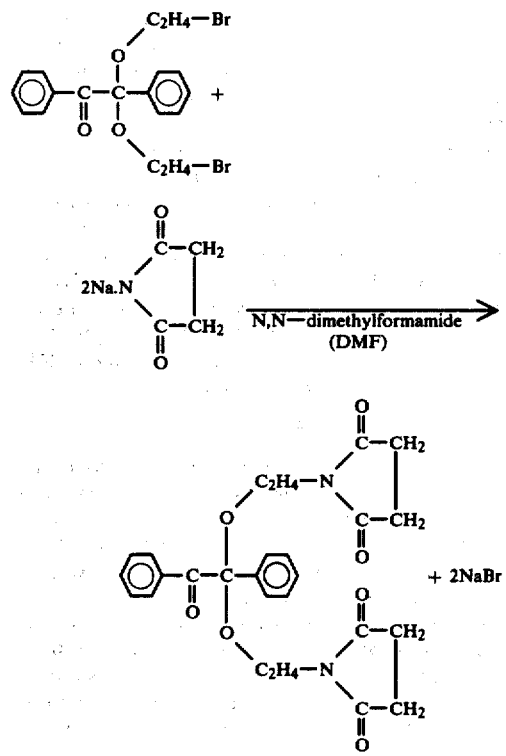

Benzil-di-($\beta$-chloroethyl)ketal can be used instead of benzil-di-($\beta$-bromoethyl)ketal.

When both $Y_1$ and $Y_2$ are hydrogen atoms, both $Z_1$ and $Z_2$ are —$C_2H_4$—, and the groups of the formula

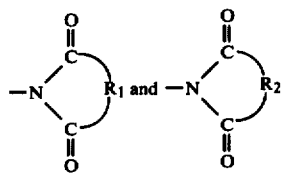

are diallylisocyanuryl groups, the compound of this invention can be similarly produced in accordance with the following reaction scheme (A').

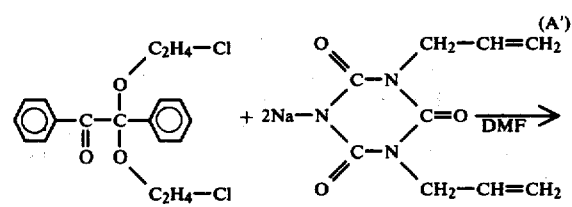

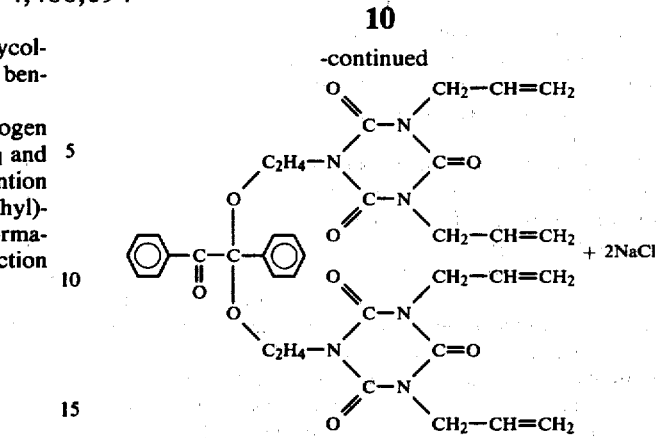

Another synthesizing procedure for the benzil ketals of this invention is the one shown by the following reaction scheme (B).

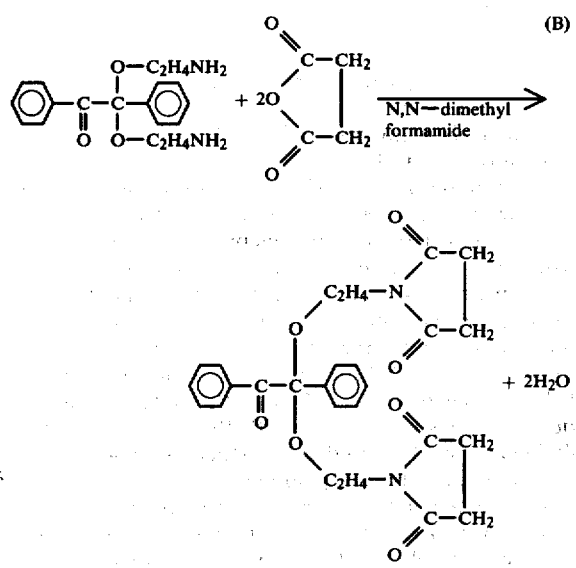

The reaction shown by scheme (B) can also be carried out easily in the absence or presence of the same reaction solvent as used in the reaction of scheme (A). under similar reaction temperature conditions.

The particular utility of the benzil ketal compound of this invention is markedly exhibited when it is used as a photopolymerization initiator in a method which comprises subjecting to ultraviolet irradiation the melt-shaped article of a photo-crosslinkable resin disclosed in the above cited U.S. Ser. No. 840,301 which has matured into U.S. Pat. No. 4,256,558 and corresponds to DOS No. 2745906.9, U.S. Ser. No. 920,834 (DOS No. 2829572.9) and U.S. Pat. No. 4,196,066, and U.S. Ser. No. 015,798 corresponding to DOS No. 2907983.2, i.e. a shaped article capable of being crosslinked under light which is prepared from a melt blend of a saturated thermoplastic resin, a crosslinking agent and a photopolymerization initiator.

When the compound of this invention is used as an initiator for a photo-crosslinking reaction of a thermoplastic resin as described above, a polyester resin is mainly used as the thermoplastic resin. The polyester resin is the one obtained by reacting a difunctional carboxylic acid or its ester-forming derivative with a diol component or its ester-forming derivative. Typical examples of the polyester resin are polyethylene terephthalate, polybutylene terephthalate, polyester elastomers, polyetherester elastomers, and polyesterester elastomers.

Instead of the polyester resins, other saturated thermoplastic resins can also be used. Examples include polyamides, polyolefins such as polyethylene and polypropylene, and polystyrene.

Suitable crosslinking agents which are incorporated in the above-exemplified saturated resins give crosslinkable resin compositions generally include aliphatic unsaturated group-containing compounds which are substantially stable under the melting conditions of the thermoplastic resins. Preferred crosslinking agents are those which contain at least two groups of the following general formulae

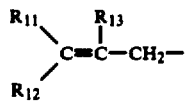 (IV)

wherein $R_{11}$, $R_{12}$ and $R_{13}$ are identical or different, and are selected from the class consisting of a hydrogen atom and alkyl groups having 1 to 6 carbon atoms, preferably H, —CH$_3$.

The groups represented by the above formula are, for example, allyl groups or substituted allyl groups. Preferred compounds which contain at least two such groups and are stable under the melting conditions of thermoplastic resins are amide compounds, imide compounds, isocyanurate ester compounds, and cyanurate ester compounds. Specific examples of these compounds include N,N'-diallyl terephthalamide, N,N'-diallyl pyromellitimide, N,N'-dimethallyl terephthalamide, triallyl isocyanurate, trimethallyl isocyanurate, triallyl cyanurate, hexamethylenebis[diallyl isocyanurate], and diallyl glycidyl isocyanurate.

It is recommended to choose the individual ingredients, i.e. a saturated thermoplastic resin, a crosslinking agent and the photopolymerization initiator of this invention, such that they can be melt-blended with each other and have good compatibility with each other.

The compound of formula (I) in accordance with this invention can also be used as a photopolymerization initiator for conventionally known photosensitive resins. Such a photosensitive resin may be a monomer containing an ethylenic double bond and a mixture of such monomers, or an unsaturated oligomer or an unsaturated polymer, or a mixture of it with the aforesaid monomer.

Examples of these photosensitive resins are mixtures of the above monomers and unsaturated polyesters frequently used to make printing plates, and compositions used in so-called UV ink. When the compound of this invention is used in such an application, the long-term storage stability of photosensitive resin compositions can be improved because of the excellent thermal stability of the aforesaid compound of this invention. Furthermore, since the compound of this invention has a very high efficiency of initiation, it can lead to the shortening of the exposure time.

The compounds of general formula (I) in accordance with this invention, either singly or as a mixture of two or more, are used in an amount of 0.01 to 20% by weight, preferably 0.1 to 10% by weight, depending upon the intended application.

When the compound of this invention is to be added to a photo-crosslinkable composition of a saturated thermoplastic resin, the above compound is blended together with a crosslinking agent under the melting conditions.

When it is added to a photopolymerizable liquid composition comprising an unsaturated monomer or polymer, the compound of this invention may simply be mixed with the composition and stirred.

The resulting sensitized composition may be insolubilized by known methods involving irradiation of actinic light. A suitable source of actinic light for irradiation of a composition containing the photopolymerization initiator of formula (I) is the one having an energy in the range of 300 to 400 m$\mu$.

The following examples illustrate the present invention in greater detail. In these examples, all parts are parts by weight. $^1$H nuclear magnetic resonance spectra were recorded on a Varian EM-360A NMR SPECTROMETER. The infrared absorption spectra were determined by a HITACHI EPI-510 (a product of Hitachi Limited). Elemental analysis was carried out by Yanagimoto MT-2 C.H.N. corder. The weight loss starting temperature was measured by RIGAKU DENKI TG-DTA Analyzer (8075D1).

EXAMPLE 1

One hundred (100) grams of benzil-di($\beta$-bromoethyl)-ketal and 60.5 g of sodium succinimide were dissolved in 500 ml of N,N-dimethylformamide (to be referred to as DMF), and the solution was heated at 50° to 60° C. for 6 hours with stirring. After the reaction, the reaction mixture was poured into 1 liter of ice water. The resulting crystals were filtered, thoroughly washed with water, and dried to afford 95 g (88% yield) of benzil-di($\beta$-succinimidoethyl)ketal as white crystals. Recrystallization from ethanol yielded crystals having a melting point of 90° to 92° C. The product is referred to as initiator 1.

| $^1$H NMR (CDCl$_3$, $\delta$) | |
|---|---|
| 2.62 (s) | 8H |
| 3.11~3.60 (m) | 4H ⎫ |
| 3.60~3.88 (m) | 4H ⎬ A$_2$B$_2$ |
| 7.1~7.66 (m) | 8H ⎭ |
| 7.80~8.03 (m) | 2H |

IR $\diagdown$C=O 1700 cm$^{-1}$ (V.S), 1770 (W)

| Elemental analysis: (%) | Cal. C; 25.26, H; 5.48, N; 5.86 |
| | Obs. C; 65.29, H; 5.27, N; 5.79 |
| Weight loss starting temperature: 277° C. | |

EXAMPLE 2

Benzil-di($\beta$-bromoethyl)ketal (8.84 g) and 7.4 g of potassium phthalimide were dissolved in 50 ml of DMF, and reacted at 50° to 60° C. for 6 hours. When the reaction mixture was poured into 100 ml of ice water, white crystals formed. The crystals were collected by filtration, well washed with water, and dried to give 11 g of benzil-di-(β-phthalimidoethyl)ketal in a yield of 96%. Recrystallization from a mixture of ethanol and chloroform afforded crystals having a melting point of 132° to 134° C. The product is referred to as initiator 2.

The spectral and analytical data of the product were as follows:

| ¹H NMR (CDCl₃, δ) | |
|---|---|
| 3.34~3.47 (m) | 4H |
| 3.70~4.03 (m) | 4H |
| 6.68~7.92 (m) | 18H |

IR $\diagup\!\!\!\!\!\diagdown$C=O 1708 cm⁻¹ (V.S), 1775 (M)

| Elemental analysis: (%) | Cal. C; 71.07, H; 4.56, N; 4.88 |
| | Obs. C; 71.03, H; 4.36, N; 4.87 |
| Weight loss starting temperature: 283° C. | |

EXAMPLE 3

Benzil-di(β-chloroethyl)ketal (13.9 g) and 19.7 g of sodium diallylisocyanurate were placed in 300 ml of DMF, and heated at 60° to 70° C. for 8 hours with stirring. The reaction mixture was poured into ice water, filtered, well washed with cold water, and dried to provide 24 g (yield 87%) of benzil-di-(β-diallylisocyanurylethyl)ketal. Recrystallization from a mixture of ethanol and chloroform yielded crystals having a melting point of 111° to 112° C. The product is referred to as initiator 3.

The spectral data of this product were as follows:

| ¹H NMR (CDCl₃, δ) | |
|---|---|
| 3.60 (t) | 4H |
| 4.20 (t) | 4H |
| 4.42 (d) | 8H |
| 5.00~6.30 (m) | 12H |
| 7.02~7.67 (m) | 8H |
| 7.77~8.02 (m) | 2H |

IR $\diagup\!\!\!\!\!\diagdown$CO= 1690 cm⁻¹ (V.S)

| Elemental analysis: (%) | Cal. C; 61.79, H; 5.62, N; 12.01 |
| | Obs. C; 61.43, H; 5.22, N; 11.77 |
| Weight loss starting temperature: 353° C. | |

EXAMPLE 4

Benzil-di-(β-bromoethyl)ketal (13.26 g) and 8.91 g of sodium glutarimide were dissolved in 50 ml of N,N-dimethylformamide, and reacted at 50° C. for 7 hours. When the reaction mixture was poured into 200 ml of ice water, white crystals formed. These crystals were washed with water, and dried to give 13.6 g of benzil-di-(β-glutarimidoethyl)ketal.

EXAMPLE 5

Benzil-di-(β-bromoethyl)ketal (9.2 g) and 13.9 g of sodium di-β-methallylisocyanurate were put into 100 ml of N,N-dimethylformamide, and reacted at 60° C. for 7 hours with stirring. The reaction mixture obtained was worked up in the same way as in Example 4 to afford 13.7 g (yield 87.3%) of benzil-di-[β-(di-β-methallylisocyanuryl)ethyl]ketal of the following formula:

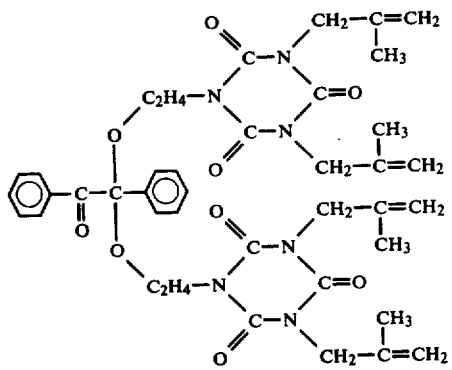

Recrystallization from a mixture of ethanol and chloroform afforded crystals having a melting point of 113° to 117° C.

EXAMPLE 6

Benzil-di-(β-bromoethyl)ketal (13.26 g) and 11.55 g of sodium hexahydrophthalimide were dissolved in 100 ml of N,N-dimethylformamide, and heated at 50° to 60° C. for 5 hours with stirring. The reaction mixture was worked up in the same way as in Example 4 to afford 16.05 g (yield 89.5%) of benzil-di-(β-hexahydrophthalimidoethyl)ketal. Recrystallization from a mixture of ethanol and chloroform afforded crystals having a melting point of 115°–116° C.

EXAMPLE 7

Benzil-di-(β-bromoethyl)ketal (13.26 g) and 11.42 g of sodium 1,2,5,6-tetrahydrophthalimide were dissolved in 100 ml of N,N-dimethylformamide, and reacted and worked up in the same way as in Example 4. There was obtained 15.3 g (yield 85.9%) of benzil-di-(β-1,2,5,6-tetrahydrophthalimidoethyl)ketal.

EXAMPLE 8

When 13.26 g of benzil-di-(β-bromoethyl)ketal and 10.63 g of sodium 3,3-dimethylglutarimide were reacted and worked up in the same way as in Example 4, 16.5 g (yield 95.8%) of benzil-di-(3,3-dimethyl glutarimidoethyl)ketal was obtained. Recrystallization from ethanol afforded crystals having a melting point of 130° C.

EXAMPLE 9

When 1.19 g of p,p'-dimethylbenzil-di-(β-bromoethyl)ketal and 1.3 g of sodium diallylisocyanurate were reacted and worked up in the same way as in Example 4, 0.55 g of p,p'-dimethylbenzil-di-(β-diallylisocyanurylethyl)ketal was obtained. Recrystallization from ethanol afforded crystals having a melting point of 133° to 134° C.

EXAMPLE 10

When 1.19 g of p,p'-dimethylbenzil-di-(β-bromoethyl)ketal and 1.11 g of potassium phthalimide were reacted and worked up in the same way as in Example 4, 0.95 g of p,p'-dimethylbenzil-di-(β-phthalimidoethyl)ketal was obtained. Recrystallization from ethanol afforded crystals having a melting point of 214° to 215° C.

SYNTHESIS EXAMPLES 1 AND 2

21 g (0.1 mole) of benzil was suspended in thionyl chloride (23.8 g; 0.2 mole), and 0.4 mole of propylene chlorohydrin or butylene chlorohydrin was added dropwise. After the addition, the mixture was stirred at room temperature for 2 hours, and then at 60° C. for 4 hours. Then, the reaction mixture was poured into 1 liter of ice water having 5 g of $K_2CO_3$ dissolved therein, and the organic layer was separated. The organic layer was washed about twice with water, and ether was added. The mixture was dried over $Na_2SO_4$ to remove the ether, and then distilled.

When propylene chlorohydrin was used, 15 g of a product was obtained at 205° to 210° C. and 0.2 to 0.3 mmHg. This product was benzil-di(γ-chloropropyl)-ketal. Its structure was determined by NMR and IR.

When butylene chlorohydrin was used, the product distilled at 213° C. at 0.25 mmHg to give 18.7 g of benzil-di-(δ-chlorobutyl)ketal. Its structure was determined by NMR and IR.

EXAMPLE 11

2.6 g of benzil-di-(γ-chloropropyl)ketal obtained in Synthesis Example 1 and 3.03 g of potassium phthalimide were reacted and worked up in the same way as in Example 4 to afford 2.72 g of benzil-di-(γ-phthalimidopropyl)ketal.

EXAMPLE 12

3.58 g of benzil-di-(γ-chloropropyl)ketal obtained in Synthesis Example 1 and 5.21 g of sodium diallylisocyanurate were reacted and worked up in the same way as in Example 4, to afford 6.1 g of benzil-di-(γ-diallylisocyanurylpropyl)ketal.

EXAMPLE 13

4.09 g of benzil-di-(δ-chlorobutyl)ketal obtained in Synthesis Example 2 and 3.03 g of potassium phthalimide were reacted and worked up in the same way as in Example 4 to afford 5 g of benzil-di-(δ-phthalimidobutyl)ketal.

EXAMPLE 14

Benzil-di-(δ-chlorobutyl)ketal (4.09 g) and 5.54 g of sodium diallylisocyanurate were reacted and worked up in the same way as in Example 4 to afford 3.75 g of benzil-di-(δ-diallylcyanurylbutyl)ketal.

The spectral and analytical data of the compounds obtained in the above Examples are tabulated in Table 1.

The numbers of the initiators shown below correspond to the numbers of the Examples.

TABLE 1

| Initiator No. | $H^1$ NMR spectrum CDCl$_3$ δ | | Infrared spectrum | $\diagdown C=O$ | Melting point °C. | Weight loss starting temperature °C. |
|---|---|---|---|---|---|---|
| 4 | 1.52~2.30 (m) | 4H | 1670 cm$^{-1}$ | (V.S) | — | 270 |
|   | 2.59 (t) | 8H | 1725 cm$^{-1}$ | (M) | | |
|   | 3.41 (t) | 4H | | | | |
|   | 4.02 (t) | 4H | | | | |
|   | 7.03~7.63 (m) | 8H | | | | |
|   | 7.80~8.08 (m) | 2H | | | | |
| 5 | 1.73 (s) | 12H | 1690 cm$^{-1}$ | (V.S) | 113~117° C. | 358 |
|   | 3.60 (t) | 4H | | | | |
|   | 4.17 (t) | 12H | | | | |
|   | 4.37 (s) | | | | | |
|   | 4.73 (b.s) | 8H | | | | |
|   | 4.84 (b.s) | | | | | |
|   | 7.10~7.60 (m) | 8H | | | | |
|   | 7.77~8.00 (m) | 2H | | | | |
| 6 | 1.20~2.18 (m) | 16H | 1690 cm$^{-1}$ | (V.S) | 115~116° C. | 270 |
|   | 2.68~2.98 (m) | 4H | 1767 cm$^{-1}$ | (W) | | |
|   | 3.33~3.87 (m) | 8H | | | | |
|   | 7.08~7.64 (m) | 8H | | | | |
|   | 7.81~8.09 (m) | 2H | | | | |
| 7 | 1.90~2.84 (m) | 8H | 1695 cm$^{-1}$ | (V.S) | — | 241 |
|   | 2.92~3.20 (m) | 4H | 1765 cm$^{-1}$ | (W) | | |
|   | 3.27~3.83 (m) | 8H A$_2$B$_2$ | | | | |
|   | 5.57~6.10 (m) | 4H | | | | |
|   | 7.00~7.60 (m) | 8H | | | | |
|   | 7.80~8.10 (m) | 2H | | | | |
| 8 | 1.03 (s) | 12H | 1670 cm$^{-1}$ | (V.S) | 160° C. | 275 |
|   | 2.48 (s) | 8H | 1725 cm$^{-1}$ | (M) | | |
|   | 3.47 (t) | 4H | | | | |
|   | 4.03 (t) | 4H | | | | |
|   | 7.07~7.67 (m) | 8H | | | | |
|   | 7.87~8.13 (m) | 2H | | | | |
| 9 | 2.00 (s) | 6H | 1710 cm$^{-1}$ | (V.S) | 133~134° C. | 331 |
|   | 2.17 (s) | | 1770 cm$^{-1}$ | (W) | | |
|   | 3.33~4.05 (m) | 8H | | | | |
|   | 6.5~8.0 (m) | 16H | | | | |
|   | 7.75 (s) | | | | | |
| 10 | 2.28 (b.s) | 6H | 1675 cm$^{-1}$ | (V.S) | 214~215° C. | higher than 265 |
|   | 3.4~3.73 (m) | 4H | | | | |
|   | 3.94~4.25 (m) | 12H | | | | |
|   | 4.39 (d) | | | | | |
|   | 5.07~6.20 (m) | 12H | | | | |

TABLE 1-continued

| Initiator No. | H¹ NMR spectrum CDCl₃ δ | | Infrared spectrum | $\diagup^{C=O}$ | Melting point °C. | Weight loss starting temperature °C. |
|---|---|---|---|---|---|---|
| 11 | 6.87~7.93 (m)<br>1.67~2.27 (m)<br>3.47 (t)<br>3.79 (t) | 8H<br>4H<br>8H | 1710 cm⁻¹<br>1768 cm⁻¹ | (V.S)<br>(M) | — | 270 |
| 12 | 7.20~8.20 (m)<br>1.63~2.24 (m)<br>3.42 (t)<br>4.02 (t)<br>4.53 (d) | 18H<br>4H<br>4H<br>4H<br>8H | 1685 cm⁻¹ | (V.S) | — | higher than 350 |
| 13 | 5.10~6.40 (m)<br>7.17~7.73 (m)<br>7.93~8.20 (m)<br>1.43~2.00 (m)<br>3.37 (t)<br>3.69 (t) | 12H<br>8H<br>2H<br>8H<br>8H | 1705 cm⁻¹<br>1768 cm⁻¹ | (V.S)<br>(M) | — | 288 |
| 14 | 7.17~8.11 (m)<br>1.33~2.07 (m)<br>3.23~3.60 (m)<br>3.73~4.14 (m)<br>4.51 (d)<br>5.10~6.47 (m)<br>7.2~7.82 (m)<br>7.97~8.27 (m) | 2H<br>8H<br>4H<br>4H<br>8H<br>12H<br>8H<br>2H | 1685 cm⁻¹ | (V.S) | — | 353 |

EXAMPLE 15

One hundred (100) parts of polyethylene terephthalate (intrinsic viscosity 0.66) was melted at 280° C., and 2 parts of hexamethylenebis[diallylisocyanurate] (an allyl-type crosslinking agent) and 1 parts of initiator No. 1 were blended in the molten state in an atmosphere of nitrogen. No fuming based on the sublimation of the initiator occurred at this time. The resulting blend was molded into chips, and then formed into a film. The film (thickness 0.5 mm) was subjected to light irradiation for 1 minute from a 2 KW high-pressure mercury lamp (30 W/cm). The light-irradiated product was dissolved at 140° C. for 30 minutes in a mixed solvent of phenol/tetrachloroethane (40/60), and the remaining insoluble matter was measured. The ratio of the insoluble residue was 50%.

COMPARATIVE EXAMPLE 1

One hundred parts of polyethylene terephthalate chips (intrinsic viscosity 0.66) was dissolved at 280° C. and 2 parts of hexamethylenebis-[diallylisocyanurate] and 1 part of benzil dimethyl ketal (Irgacure 651, a product of Ciba-Geigy) as an initiator were blended in the molten state in an atmosphere of nitrogen. At this time, there was heavy smoking owing to the sublimation of the initiator, to pollute the air in the working site. The resulting blend was molded into chips, formed into a film, and subjected to irradiation of light under the same conditions as in Example 15. The ratio of the residue insoluble in the above mixed solvent of phenol/tetrachloroethane (40/60) was measured. The ratio of the insoluble residue was 3%. This shows that the initiator scattered by sublimation, and could not be effectively utilized.

EXAMPLE 16

One hundred parts of Teijin ® Tevista ®I type resin not containing a photopolymerization initiator (a liquid photosensitive resin of unsaturated polyester) was blended with 1 part of initiator No. 1 at room temperature, and after defoaming, the blend was made into a printing plate by Teijin ® Tevista ® plate-making machine KJS-E type. When the plate-making was performed using a test chart, a printing plate having the desired properties was obtained by exposure for 4 minutes.

COMPARATIVE EXAMPLE 2

Example 16 was repeated except that benzoin ethyl ether was used as a polymerization initiator.

An exposure time of 8 minutes was required in order to obtain the desired plate properties.

EXAMPLE 17

One thousand (1000) parts of Teijin ® Tevista ®I type resin not containing a photopolymerization initiator (a photosensitive liquid unsaturated polyester resin) was blended with 10 parts of initiator No. 1. After defoaming, the blend was filled into a 1-liter can, and allowed to stand for one year in a laboratory at room temperature. When a printing plate was made from the blend after storing the blend for one year, the initial properties of the blend were not at all impaired even after a lapse of one year.

COMPARATIVE EXAMPLE 3

Example 17 was repeated except that benzoin ethyl ether was used as an initiator. On standing at room temperature, the plate properties of the resulting printing plate began to be deteriorated after a lapse of half a year. On standing for one year, the properties of the plate were considerably deteriorated.

EXAMPLE 18

One hundred parts of a polyester elastomer (reduced specific viscosity 2.82) derived from terephthalic acid as an acid component and a glycol component composed of 19 mole% of polytetramethylene glycol having a molecular weight of about 2000 (about 66% by weight of the entire polymer), 27 mole% of ethylene glycol and 54 mole% of tetramethylene glycol, all based on the terephthalic acid, was melted and kneaded with 2 parts of hexemethylenebis[diallyl isocyanurate] and 1 part of an initiator of the following formula in an S-type blender at 240° C. in an atmosphere of nitrogen.

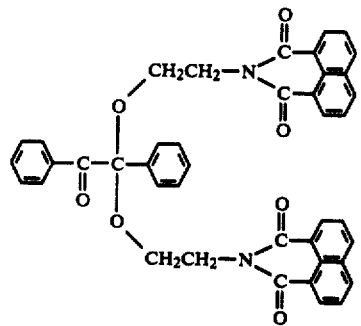

No fuming owing to the sublimation of the initiator occurred at this time. The resulting kneaded mixture was extruded from a T-die to form a film having a thickness of 400 microns. The film was subjected to irradiation of light at 90° C. for 1 minute from a 2 KW high-pressure mercury lamp (30 W/cm). The irradiated film was placed in a mixed solvent of phenol/tetrachloroethane (40/60), and dissolved at 140° C. for 30 minutes. The ratio of the insoluble residue was 84%.

EXAMPLE 19

One hundred parts of nylon 6 (having an inherent viscosity in m-cresol of 1.0), 2 parts of hexamethylenebis[diallyl isocyanurate], and 1 part by weight of an initiator of the following formula were melted and kneaded in an S-type blender at 280° C. in an atmosphere of nitrogen. At this time, no fuming owing to the sublimation of the initiator occurred. The resulting kneaded mixture was extruded from a T-die to form a film having a thickness of 400 microns. The film was subjected to irradiation of light at 60° C. for 1 minute from a 2 KW high-pressure mercury lamp (30 W/cm). The irradiated film was put into m-cresol, and dissolved. The ratio of the insoluble residue was 35%.

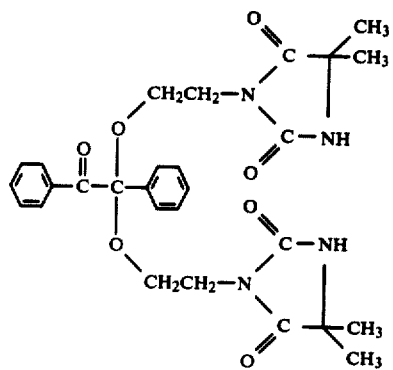

EXAMPLE 20

One hundred parts of low-pressure polyethylene, 2 parts of hexamethylene-bis[diallyl isocyanurate] and 1 part of an initiator of the following formula were melted and kneaded in an S-type blender at 220° C. in an atmosphere of nitrogen. Then, the blend was extruded through a T-die to form a film having a thickness of 400 microns. The film was subjected to irradiation of light at room temperature for 1 minute from a 2 KW high-pressure mercury lamp (30 W/cm) to form a crosslinked film.

The crosslinked film was heated in decalin, but did not at all dissolve in it.

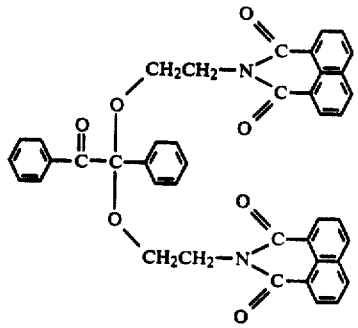

What we claim is:
1. A benzil ketal derivative of the following general formula:

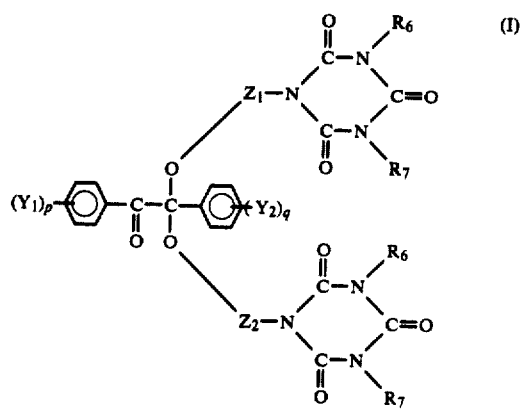

wherein $Y_1$ and $Y_2$ are identical or different, and each represents a group selected from the class consisting of a hydrogen atom, an alkyl group having 1 to 10 carbon atoms, an aryl group having 6 to 12 carbon atoms, an alkoxy group having 1 to 10 carbon atoms and a halogen atom; p and q, independently of each other, are integers of 1 to 3; $Z_1$ and $Z_2$ are identical or different and represent a group shown by the following formula:

$$-(CH_2)_m-Q-(CH_2)_n-$$

wherein Q represents

—O—, —S—, or a bond, m and n are integers of 1 to 3, and $R_3$ and
$R_4$ represent a hydrogen atom or a methyl group; and
$R_6$ and $R_7$ are identical or different and represent a hydrogen atom, an alkyl group having 1 to 5 carbon atoms, $-CH_2-CH=CH_2$,

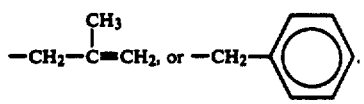

2. The compound of claim 1 wherein Q represents a bond or

wherein $R_3$ and $R_4$ are identical or different and represent a hydrogen atom or a methyl group.

3. The compound of claim 1 which is benzil-di-($\beta$-diallylisocyanurylethyl)ketal.

4. The compound of claim 1 which is benzil-di-($\beta$-dimethyallylisocyanurylethyl)ketal.

5. The compound of claim 1 which is p,p-dimethylbenzil-di-($\beta$-diallylisocyanurylethyl)ketal.

6. The compound of claim 1 which is p,p'-dimethoxybenzil-di-($\beta$-diallylisocyanurylethyl)ketal.

7. The compound of claim 1 which is benzil-di-($\beta$-dimethylisocyanurylethyl)ketal.

8. The compound of claim 1 which is benzil-di-($\beta$-diphenylisocyanurylethyl)ketal.

9. The compound of claim 1 which is benzil-di-($\beta$-dibenzylisocyanurylethyl)ketal having the formula

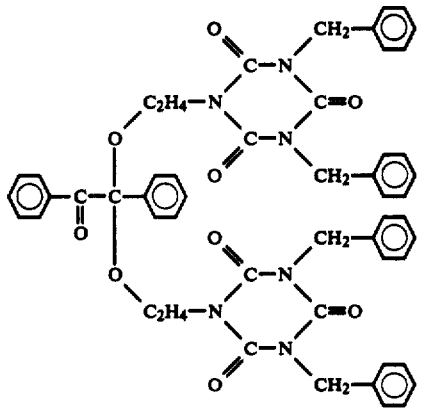

10. The compound of claim 1 which is benzil-di-($\beta$-methylethylisocyanurylethyl)ketal.

11. The compound of claim 1 which is benzil-($\beta$-diallylisocyanurylethyl, $\beta$-dimethylisocyanurylethyl)ketal.

12. The compound of claim 1 which is benzil-($\beta$-diallylisocyanurylethyl, $\beta$-dimethyallylisocyanurylethyl)ketal having the formula

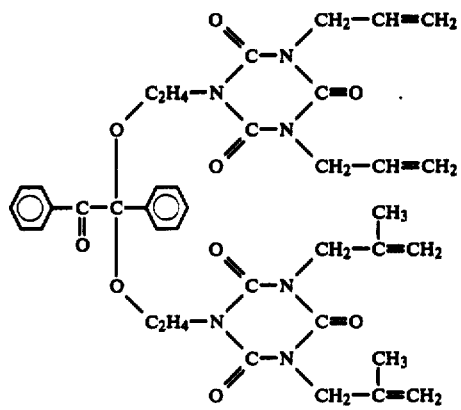

13. The compound of claim 1 which is benzil-di($\gamma$-diallylisocyanurylpropyl)ketal.

14. The compound of claim 1 which is benzil-di-($\delta$-diallylisocyanurylbutyl)ketal.

* * * * *